US009924861B2

(12) United States Patent
Gonzalez Garcia et al.

(10) Patent No.: US 9,924,861 B2
(45) Date of Patent: Mar. 27, 2018

(54) SYSTEM AND METHODS FOR ASSESSING VISION USING A COMPUTING DEVICE

(71) Applicants: Alberto O. Gonzalez Garcia, Randolph, NJ (US); Luis Perez Sanchez, Bologna (IT)

(72) Inventors: Alberto O. Gonzalez Garcia, Randolph, NJ (US); Luis Perez Sanchez, Bologna (IT)

(73) Assignees: Alberto O. Gonzalez Garcia, Randolph, NJ (US); Luis Perez Sanchez, Bologna (IT)

( * ) Notice: Subject to any disclaimer, the term of this patent is extended or adjusted under 35 U.S.C. 154(b) by 23 days.

(21) Appl. No.: 15/135,085

(22) Filed: Apr. 21, 2016

(65) Prior Publication Data

US 2016/0309998 A1 Oct. 27, 2016

Related U.S. Application Data

(60) Provisional application No. 62/150,400, filed on Apr. 21, 2015.

(51) Int. Cl.
*A61B 3/02* (2006.01)
*A61B 3/11* (2006.01)
(Continued)

(52) U.S. Cl.
CPC .............. *A61B 3/02* (2013.01); *A61B 3/0041* (2013.01); *A61B 3/0083* (2013.01); *A61B 3/11* (2013.01);
(Continued)

(58) Field of Classification Search
CPC .. A61B 3/10; A61B 3/11; A61B 3/111; A61B 3/0041; A61B 3/02; A61B 3/113;
(Continued)

(56) References Cited

U.S. PATENT DOCUMENTS 6,068,378 A 5/2000 Weiss
6,648,820 B1 * 11/2003 Sarel .................... A61B 5/0002
128/903
(Continued)

OTHER PUBLICATIONS

International Search Report and Written Opinion, PCT/US2016/028645, dated Jul. 27, 2016.

*Primary Examiner* — Jordan Schwartz
(74) *Attorney, Agent, or Firm* — Entralta P.C.; Justin G. Sanders; Peter D. Weinstein

(57) ABSTRACT

A system and associated methods are disclosed for objectively assessing the vision of a user using a computing device. In at least one embodiment, upon an assessment application in memory on the computing device being initialized, a baseline profile is established for the user based on a current state of an at least one visual parameter associated with a display screen of the computing device. The assessment application selectively modifies the at least one visual parameter periodically, and then monitors and records the user's response to the modifications. The user's responses are compared to the baseline profile and, upon the responses exceeding a pre-defined threshold Delta value, the assessment application notifies the user of a possible change in their vision.

17 Claims, 2 Drawing Sheets

(51) Int. Cl.
  *A61B 3/14* (2006.01)
  *A61B 3/00* (2006.01)
  *A61B 3/113* (2006.01)
  *A61B 3/15* (2006.01)

(52) U.S. Cl.
  CPC .............. *A61B 3/111* (2013.01); *A61B 3/113* (2013.01); *A61B 3/14* (2013.01); *A61B 3/152* (2013.01)

(58) Field of Classification Search
  CPC ......... A61B 3/022; A61B 3/028; A61B 3/032; A61B 3/06; A61B 3/063; A61B 3/14

See application file for complete search history.

(56) References Cited

U.S. PATENT DOCUMENTS

| | | | |
|---|---|---|---|
| 7,918,558 B1* | 4/2011 | Legerton | A61B 3/0033 351/211 |
| 2003/0223038 A1* | 12/2003 | Alster | A61B 3/032 351/211 |
| 2011/0228227 A1 | 9/2011 | Roser | |
| 2012/0141970 A1 | 6/2012 | Pompilio et al. | |
| 2013/0176534 A1* | 7/2013 | Frankfort | A61B 3/113 351/209 |
| 2013/0201452 A1* | 8/2013 | Crabb | A61B 3/024 351/224 |
| 2015/0313457 A1* | 11/2015 | Kalloniatis | A61B 3/024 600/558 |
| 2016/0166204 A1* | 6/2016 | Stevens | A61B 3/113 600/558 |
| 2017/0143202 A1* | 5/2017 | Palanker | A61B 3/0025 |
| 2017/0177166 A1* | 6/2017 | Kockan | G06F 3/0481 |

* cited by examiner

SYSTEM AND METHODS FOR ASSESSING VISION USING A COMPUTING DEVICE

RELATED APPLICATIONS

This application claims priority and is entitled to the filing date of U.S. provisional application Ser. No. 62/150,400, filed on Apr. 21, 2015. The contents of the aforementioned application are incorporated herein by reference.

BACKGROUND

The subject of this patent application is generally related to vision assessment, and more particularly to a system and associated methods for objectively assessing vision using a computing device.

Applicant(s) hereby incorporate herein by reference any and all patents and published patent applications cited or referred to in this application.

By way of background, the human visual system is the part of the central nervous system which gives the ability to process visual detail, as well as enables the formation of several non-image photo response functions. It detects and interprets information from visible light in order to build a representation of the surrounding environment. The visual system carries out a number of complex tasks, including the reception of light and the formation of monocular representations; the buildup of a nuclear binocular perception from a pair of two dimensional projections; the identification and categorization of visual objects; assessing distances to and between objects; and guiding body movements in relation to visual objects. Traditional methods used for assessing a patient's visual functions require the involvement of a trained human physician (or physician's assistant). As such, these methods tend to be either completely manual or semi-automated at best. Relatedly, relying upon a physician to perform such assessments requires that a patient actually make an appointment with their physician, hoping then that such periodically scheduled assessments are serendipitously timed so as to catch a vision-related disease at a relatively early stage. Furthermore, these traditional visual assessment methods require the active, conscious and subjective participation of the patient. As a result, the assessments suffer from a risk of being strongly influenced by the voluntary (or involuntary) and subjective responses of the patient. Additionally, traditional assessment methods tend to constitute a cross-sectional evaluation of visual function with separated results rather than a compendium of these visual parameters and its multivariate analysis.

Aspects of the present invention are directed to solving all of these problems by providing a system and associated methods for assessing vision using a computing device, as discussed in detail below.

SUMMARY

Aspects of the present invention teach certain benefits in construction and use which give rise to the exemplary advantages described below.

The present invention solves the problems described above by providing a system and associated methods for continuously and objectively assessing the vision of a user using a computing device in possession of the user. In at least one embodiment, upon an assessment application in memory on the computing device being initialized, a baseline profile is established for the user based on a current state of an at least one visual parameter associated with a display screen of the user device. The assessment application selectively modifies the at least one visual parameter periodically, and then monitors and records the user's response to the modifications. The user's responses are compared to the baseline profile and, upon the responses exceeding a pre-defined threshold Delta value, the assessment application notifies the user of a possible change in their vision.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION

Figure 1:
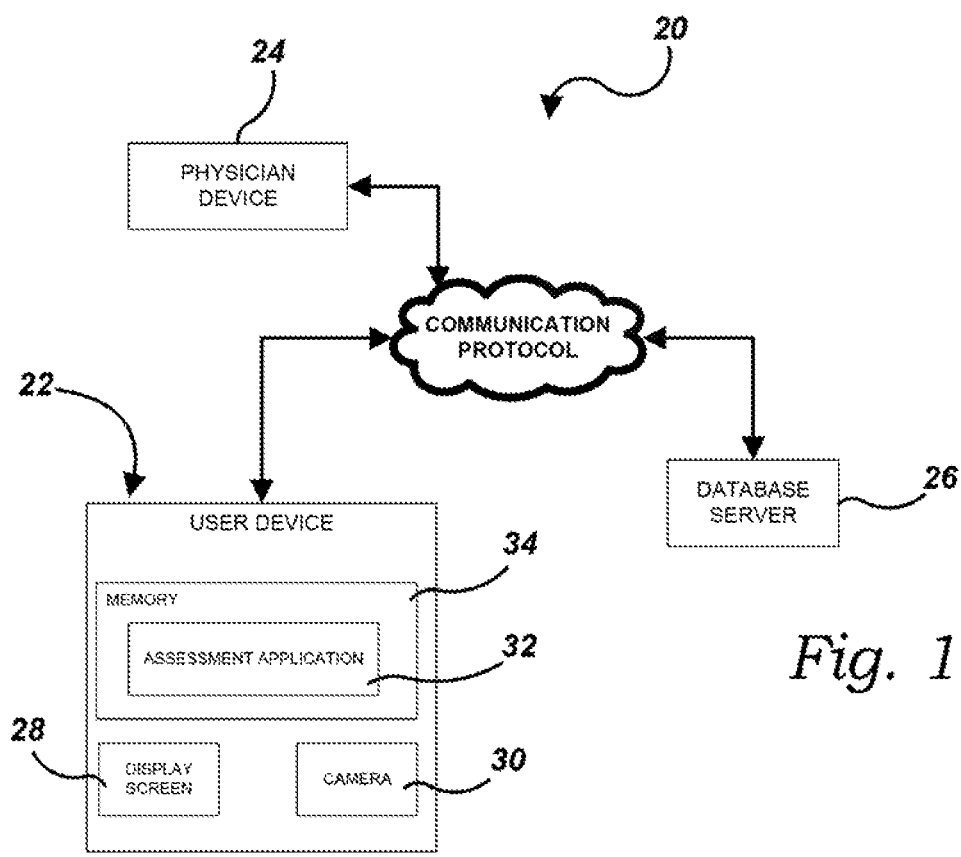
FIG. 1 is a simplified schematic view of an exemplary vision assessment system, in accordance with at least one embodiment.

Turning now to FIG. 1, there is shown a simplified schematic view of an exemplary vision assessment system 20. The system 20 provides, in at least one embodiment, an at least one user device 22 configured for receiving and processing select data used to assess the vision of a user of the user device 22. In at least one embodiment, the system 20 also provides an at least one physician device 24 in selective communication with the user device 22, the purpose of which is discussed further below. Additionally, in at least one embodiment, the system 20 also provides an at least one database server 26 in communication with the user device 22 and configured for selectively storing data obtained by the user device 22, along with certain other data as discussed further below. In at least one embodiment, the user device 22 and database server 26 are one and the same, with the database server 26 residing in memory on the user device 22.

At the outset, it should be noted that communication between each of the at least one user device 22, at least one physician device 24, and at least one database server 26 may be achieved using any wired- or wireless-based communication protocol (or combination of protocols) now known or later developed. As such, the present invention should not be read as being limited to any one particular type of communication protocol, even though certain exemplary protocols may be mentioned herein for illustrative purposes. It should also be noted that the terms "user device" and "physician device" are intended to include any type of computing or electronic device now known or later developed, such as desktop computers, mobile phones, smartphones, laptop computers, tablet computers, personal data assistants, gaming devices, POS systems, vending machines, unattended terminals, access control devices, point of interaction ("POI") systems, etc. It should also be noted that, in at least one embodiment, the term "physician" is intended to generally include any type of medical professional or medical entity for which the user has provided prior authorization to receive vision assessment data from the user device 22.

With continued reference to FIG. 1, in at least one embodiment, the user device 22 contains the hardware and software necessary to carry out the exemplary methods for assessing the user's vision as described herein. In at least one embodiment, the user device 22 provides a display screen 28, an at least one camera 30, and a microphone (not shown). In at least one such embodiment, the at least one camera 30 is appropriately positioned on the user device 22. In an alternate embodiment, the at least one camera 30 is positioned elsewhere—either still local to the user device 22 or remotely. In at least one embodiment, the user device 22 also provides an assessment application 32 residing in memory 34 on the user device 22 and configured for running as a background process while other applications run on the user device 22—either as a standalone process running on the user device 22, or as an embedded process within another running application on the user device 22, such as an Internet browser plug-in for example. In at least one embodiment, the assessment application 32 is configured for running as a primary application on the user device 22. It should be noted that the term "memory" is intended to include any type of electronic storage medium (or combination of storage mediums) now known or later developed, such as local hard drives, solid state drives, RAM, flash memory, secure digital ("SD") cards, external storage devices, network or cloud storage devices, integrated circuits, etc. Furthermore, the various components of the user device 22 may reside in memory on a single computing or electronic device, or may separately reside on two or more computing or electronic devices in communication with one another. In at least one embodiment, the user device 22 is in the possession of a user who is desirous of having their vision automatically assessed as described further below. Similarly, in at least one embodiment, the at least one physician device 24 is in the possession or control of a participating physician whom the user has previously chosen to receive vision assessment data from the user device 22. In at least one further embodiment, the user device 22 also provides an at least one microphone (not shown) configured for allowing the user to provide voice commands to the various applications that are running on the user device 22. In at least one such further embodiment, the assessment application 32 is also configured for monitoring any audio input that is received by the microphone.

In use, in at least one embodiment, the system 20 utilizes the user device 22 and associated methods for automatically obtaining select physiognomic measurements and visual parameters of the user's vision—including but not limited to visual acuity/spatial resolution, color contrast, contrast sensitivity, contrast resolution, color vision, stereopsis, visual field, and motion detection—in order to achieve early detection of potential visual dysfunctions.

Figure 2:
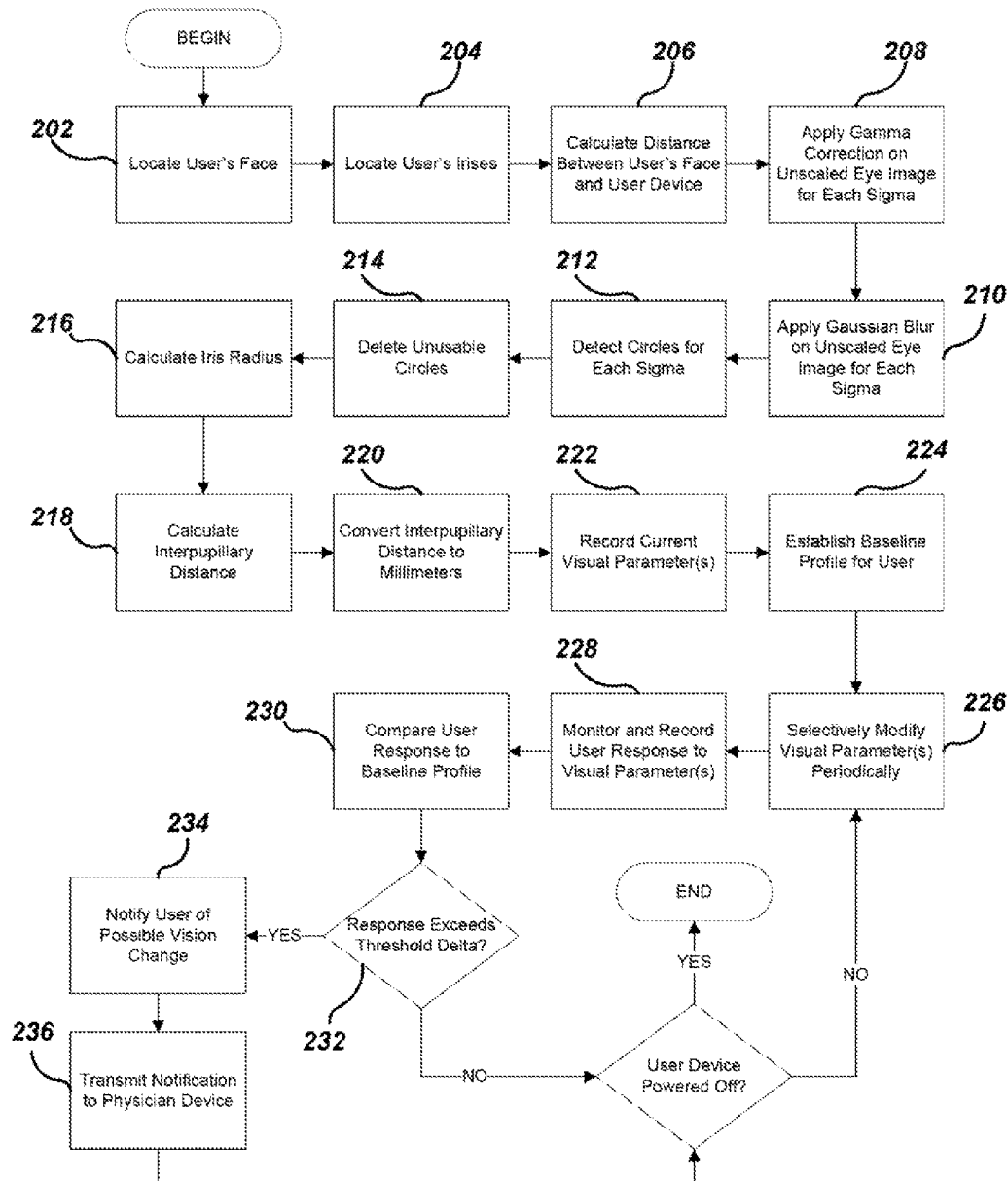
FIG. 2 is a flow diagram of an exemplary method for assessing vision using a computing device, in accordance with at least one embodiment.

In a bit more detail, in at least one embodiment, as illustrated in the flow diagram of FIG. 2, the system 20 (via the assessment application 32 running in the background on the user device 22, as discussed above) automatically measures an interpupillary distance of the user—i.e., the distance between the centers of the pupils of the two eyes of the user. In at least one such embodiment, with the user holding the user device 22 in a relatively steady position, the assessment application 32 uses a facial and/or eye pattern recognition algorithm to calculate the distance between the user's eyes and the user device 22, which data is then used in calculating the interpupillary distance. In at least one such embodiment, this is achieved by first locating and detecting the user's face (202) using known detection algorithms such as the open source CascadeClassifier provided by OpenCV. The iris of each eye is then detected (204), also using known detection algorithms such as CascadeClassifier. Given that iris diameters tend to be very consistent from one individual to another, this condition makes the iris diameter a reliable reference for calculating things like the distance between the user's eyes, as well as the height of the user's face. Specifically, an iris has an almost invariant diameter of approximately 10-12 millimeters. It should be noted that, in further embodiments, any other methods for detecting the user's face and/or irises, now known or later developed, may be substituted. With this data, in at least one embodiment, the distance between the camera of the user device and the user's face/eyes can be calculated (206) using the following formula:

$$\text{Distance to Device} = \frac{\text{FOCAL\_LENGTH} * \text{KNOWN\_FACEHEIGHT} * \text{NORMAL\_HEIGHT}}{\text{FACE\_HEIGHT} * \text{SENSOR\_HEIGHT}}$$

where the FOCAL_LENGTH value is the focal length of the camera 30, the KNOWN_FACEHEIGHT value is the estimated height of the user's face, the NORMAL_HEIGHT value is a normalization value used to avoid different resolution problems, the FACE_HEIGHT value is a computed face height in real time, and the SENSOR_HEIGHT value is the height of the camera 30 in millimeters.

With continued reference to FIG. 2, in at least one embodiment, the assessment application 32 then uses the detected iris of each eye, an unscaled eye image obtained by the camera 30 of the user device 22, an array of sigmas (used in Gaussian blur), and an array of thresholds as inputs. For each sigma, the assessment application 32 applies a gamma correction on the unscaled eye image (208), applies a Gaussian blur on the unscaled eye image using the sigma as a parameter (210), and, for each threshold, detects circles using the HoughCircles method provided by OpenCV using the threshold as a parameter (212), then deletes all circles that are determined to be too small, too big, or too far away from the iris (214). Based on that collected and calculated data, the assessment application 32 calculates the radius of the iris by calculating the median of the radiuses of the remaining circles (216).

With the centers of each iris located, such that select corresponding points on each iris may be compared and measured, the assessment application 32 then calculates the distance between the centers of each iris (i.e., the "interpupillary distance") (218), taking into account the previously calculated distance between the user's eyes and the user device 22. The calculated distance is then converted from pixels to a standard unit of measurement (220), such as millimeters. In at least one such embodiment, the assessment application 32 accomplishes this by selecting a reference object of known dimensions inside the image of the user obtained by the camera 30 of the user device 22. In the exemplary embodiment, the reference object is the iris of the user, given that an iris has an almost invariant diameter of approximately 10-12 millimeters. Using the known dimensions of the selected reference object, the distance can be converted to the desired unit of measurement (such as millimeters) using the following formula:

$$D_{mm} = O_{mm} * \frac{D_p}{O_p}$$

where $D_{mm}$ is the interpupillary distance in millimeters, $O_{mm}$ is the known size of the selected reference object in millimeters, $D_p$ is the interpupillary distance in pixels, and $O_p$ is the known size of the reference object in pixels.

In at least one embodiment, the system 20 (via the assessment application 32 running in the background on the user device 22, as discussed above) is also capable of automatically detecting whether the user is wearing eyeglasses. In at least one such embodiment, upon detecting the presence of eyeglasses, the assessment application 32 is capable of automatically calculating an optical axis of each lens of the eyeglasses, matching the center of each iris with the optical axis of the corresponding eyeglasses lens, calculating a deviation (if any) between the center of each iris and the optical axis of the corresponding eyeglasses lens, determining whether the de-centered lenses are related with frame position, and determining whether the de-centered lenses are related with a misalignment of the nose bridge pads of the eyeglasses.

In at least one embodiment, as discussed further below, the assessment application 32 also utilizes the various features of the user device 22 (i.e., screen luminosity, zoom, contrast, etc.) to evaluate the user's vision, based on the user's particular interactions with said features. Thus, in at least one embodiment, the system 20 is capable of automatically tracking and recording possible changes in the user's vision over time without requiring the active/conscious interaction of the user. In a bit more detail, in at least one embodiment, upon the assessment application 32 being initialized or executed for the first time on the user device 22, the assessment application 32 first records the current state of an at least one visual parameter associated with the display screen 28 of the user device 22 (222)—i.e., font size, font type, screen luminosity, contrast, etc.—and establishes a baseline profile of the associated user based on those current visual parameter details (224). In at least one such embodiment, the baseline profile includes values for one or more of the following visual parameters: visual acuity (i.e., spatial resolution); contrast sensitivity (i.e., contrast); color sensitivity (i.e., chromatic resolution); and visual field (i.e., perimetry).

In a bit more detail, in at least one embodiment, and by way of example, with respect to the visual acuity parameter, the assessment application 32 presents text displayed on the display screen 28 in different types/sizes/zooms—as the user attempts to adjust the text/font type and/or size, the assessment application 32 records the average font size and zoom the user chooses for their daily reading tasks. In at least one such embodiment, given that a particular font size may vary from one user device 22 to another (depending on the size and resolution of the display screen 28, among other variables), the font size is normalized using the following formula:

Normalized Size=FONT_SIZE*DEVICE_PIXEL_RATIO*DEVICE_ZOOM where the FONT_SIZE value is the numerical font size of the text displayed on the user device 22, the DEVICE_PIXEL_RATIO value is a ratio between the device-independent pixels and the pixels of the user device 22, and the DEVICE_ZOOM value is a zoom factor (if any) that the user may selectively utilize for viewing the text in a relatively larger size on the display screen 28. Thus, in at least one such embodiment, the user application 32 is able to determine a reasonably precise measure of the text that the user is reading on the display screen 28. In at least one embodiment, this same formula may be inverted in order to determine and recommend a particular font size based on the user's history.

With respect to the contrast sensitivity parameter, in at least one embodiment, the assessment application 32 presents text having different levels of screen luminance, with the screen luminance being based on the luminosity of the surrounding environment—as the user attempts to adjust the screen luminance, the assessment application 32 records the average screen luminance the user chooses for their daily reading tasks. In at least one embodiment, contrast resolution is determined using the following formula:

$$\text{Contrast Resolution} = \frac{\max\left(\frac{\text{FONT\_LUMINANCE}}{\text{BG\_LUMINANCE}}\right) + 0.05}{\min\left(\frac{\text{FONT\_LUMINANCE}}{\text{BG\_LUMINANCE}}\right) + 0.05} - 1$$

where the FONT_LUMINANCE value is a relative luminance of the current font color, and the BG_LUMINANCE value is a relative luminance of the current background color.

With respect to the color sensitivity parameter, in at least one embodiment, the assessment application 32 presents text having different colors, with the text being overlaid on backgrounds of different colors—as the user attempts to adjust each of the text color and background color, the assessment application 32 records the average text color and background color the user chooses for their daily reading tasks.

With respect to the visual field parameter, in at least one embodiment, the assessment application 32 changes the characters of a given selection of text the same color and luminance as the background—in other words, the characters of a given selection of text are selectively and temporarily made invisible. In one such embodiment, the characters in a given selection of text are sequentially (i.e., from left to right, or right to left) made invisible and then visible once more, which creates a movement sensation and, thus, a visual field stimulus. By using the camera, the assessment application 32 can detect the attempt of the user (gaze recognition) to look at the location on the display screen 28 being stimulated. The speed of reading is another parameter that is calculated to aim in the vision assessment and a previously calculated speed of reading, is compared with subsequent speed measurements. Another way of analyzing visual function is the combined testing of said parameters (i.e. spatial frequency combined with contrast sensitivity, for example).

After establishing the baseline profile, the assessment application 32 then selectively modifies the at least one visual parameter periodically (226)—i.e., increase/decrease font sizes, increase/decrease screen luminosity, increase/decrease contrast, etc. In at least one embodiment, the screen luminosity is also selectively adjusted—either by the assessment application 32, another application running on the user device 22, or an operating system of the user device 22—based on the luminosity of the surrounding environment. The visual parameters themselves may be located in any software application, now known or later developed, capable of running on the user device 22—i.e., Internet browsers, text editors, spreadsheet applications, presentation applications, photo editing software, etc. The visual parameter modifications are applied subtly, randomly, and sporadically in order to better avoid user predictability. Once applied, the assessment application 32 monitors and records the user's response to the modification(s) (228)—i.e., either re-adjusting the at least one visual parameter or leaving it as-is. In at least one embodiment, in addition to selectively modifying visual parameters, the assessment application 32 also monitors and records the user's unprovoked modification of visual parameters—i.e., visual parameters that were not previously modified by the assessment application 32. This recorded data is stored and compared to the data associated with the baseline profile (230). In at least one embodiment, each visual parameter is linked to or otherwise associated with a specific visual function—for example, font size is linked to visual acuity, display screen 28 contrast and luminosity are linked to human contrast sensitivity, etc. Thus, a change with respect to a particular visual parameter allows the assessment application 32 to better detect a particular type of visual function issue. This process of selectively modifying the at least one visual parameter periodically, and subsequently monitoring and recording the user's response to the modifications, continues for as long as the assessment application 32 is running on the user device 22. Upon any changes in a particular visual parameter exceeding a pre-defined threshold Delta value (232)—thus, indicating a possible visual impairment—the assessment application 32 notifies the user of the possible change in their vision (234) and suggests that they contact their physician to schedule an examination. In at least one embodiment, where the system 20 incorporates the physician device 24, the assessment application 32 may automatically transmit the notification to the physician device 24 (236). In at least one embodiment, the user application 32 also provides the user with reporting capabilities, allowing the user to selectively view their historical visual statistics and any changes in vision.

In at least one embodiment, the assessment application 32 utilizes the at least one camera 30 to monitor the distance between the user's face and the user device 22, given that holding the user device 22 relatively closer to or further from the user's face can be indicative of weakening eyesight. Accordingly, with respect to visual acuity, in at least one embodiment, rather than only monitoring changes in font size, the assessment application 32 will also monitor the distance between the user's face and the user device 22. Thus, the distance between the user's face and the camera 30 is used as a constant to adjust the calculation of the visual parameters.

In at least one embodiment, the assessment application 32 also monitors and records the user's reading speed across various combinations of visual parameters, which allows for trend analysis in order to detect any possible visual changes over time.

Aspects of the present specification may also be described as follows:

1. A method for objectively assessing the vision of a user using a computing device in the possession of said user, the method comprising the steps of: implementing an assessment application in memory on the computing device; upon the assessment application being initialized on the computing device, establishing a baseline profile for the user based on a current state of an at least one visual parameter associated with a display screen of the computing device; selectively modifying the at least one visual parameter periodically; monitoring and recording the user's response to said modifications of the at least one visual parameter; comparing the user's response to said modifications of the at least one visual parameter with the baseline profile; and upon the user's response to said modifications of the at least one visual parameter exceeding a pre-defined threshold Delta value, notifying the user of a possible change in their vision.

2. The method according to embodiment 1, wherein the step of implementing an assessment application further comprises the step of implementing the assessment application to run as a background process while an at least one other application runs on the computing device.

3. The method according to embodiments 1-2, further comprising the step of calculating a distance between the computing device and an at least one eye of the user using an at least one camera in communication with the computing device.

4. The method according to embodiments 1-3, wherein the step of calculating a distance between the computing device and an at least one eye of the user further comprises the steps of: detecting a face of the user; detecting an iris of each eye of the user; calculating a distance between the camera and the face of the user; locating a center of each iris, such that a select at least one corresponding point on each iris may be compared and measured; calculating a distance between the center of each iris; and converting the calculated distance into a standard unit of measurement using a reference object of known dimensions inside an unscaled image of an eye of the user obtained by the at least one camera.

5. The method according to embodiments 1-4, wherein the step of calculating a distance between the camera and the face of the user further comprises the step of multiplying a focal length of the camera by an estimated height of the user's face by a resolution normalization value, and dividing the resulting product by the product of a computed face height of the user's face and a height of the camera.

6. The method according to embodiments 1-5, wherein the step of locating a center of each iris further comprises the steps of: obtaining an unscaled image of an eye of the user using the at least one camera; applying a gamma correction on the unscaled eye image; applying a Gaussian blur on the unscaled eye image; detecting circles in the unscaled eye image; deleting all circles determined to be too small, too big, or too far away from the iris; and calculating the radius of the iris by calculating the median of the radiuses of the remaining circles.

7. The method according to embodiments 1-6, wherein the step of converting the calculated distance into a standard unit of measurement further comprises the step of using a reference object of known dimensions inside an unscaled image of an eye of the user obtained by the at least one camera.

8. The method according to embodiments 1-7, wherein the step of using a reference object of known dimensions inside an unscaled image of an eye of the user further comprises the step of using the iris of the user.

9. The method according to embodiments 1-8, wherein the step of converting the calculated distance into a standard unit of measurement further comprises the step of multiplying the known size of the selected reference object in millimeters by the quotient of the interpupillary distance in pixels divided by the known size of the reference object in pixels.

10. The method according to embodiments 1-9, further comprising the steps of, upon detecting the presence of eyeglasses: calculating an optical axis of each lens of the eyeglasses; matching a center of each iris with the optical axis of the corresponding eyeglasses lens; and upon determining that a deviation exists between the center of each iris and the optical axis of the corresponding eyeglasses lens: determining whether the de-centered lenses are related to frame position; and determining whether the de-centered lenses are related to a misalignment of the nose bridge pads of the eyeglasses.

11. The method according to embodiments 1-10, wherein the step of establishing a baseline profile for the user based on a current state of an at least one visual parameter associated with a display screen of the computing device, further comprises the step of recording the current state of at least one of a visual parameter indicative of visual acuity, a visual parameter indicative of contrast sensitivity, a visual parameter indicative of color sensitivity, and a visual parameter indicative of visual field.

12. The method according to embodiments 1-11, wherein the step of recording the current state of a visual parameter indicative of visual acuity further comprises the step of recording at least one of a current font type, a current font size, and a current device zoom.

13. The method according to embodiments 1-12, further comprising the step of normalizing the font size by multiplying a numerical font size by a ratio between device-independent pixels and pixels of the computing device, by the device zoom.

14. The method according to embodiments 1-13, wherein the step of recording the current state of a visual parameter indicative of contrast sensitivity further comprises the step of recording a screen luminance of the display screen of the computing device.

15. The method according to embodiments 1-14, further comprising the step of determining a contrast resolution of the display screen by: calculating first quotient by dividing the greater of a relative luminance of a current font color and a relative luminance of a current background color, plus a value of 0.05, by the lesser of the relative luminance of the current font color and the relative luminance of the current background color, plus a value of 0.05; and calculating the contrast resolution by dividing the first quotient, minus a value of 1, by a value of 20.

16. The method according to embodiments 1-15, wherein the step of recording the current state of a visual parameter indicative of color sensitivity further comprises the step of recording a current font color and a current background color.

17. The method according to embodiments 1-16, wherein the step of recording the current state of a visual parameter indicative of visual field further comprises the step of temporarily hiding select of a given selection of text.

18. The method according to embodiments 1-17, wherein the step of temporarily hiding select of a given selection of text further comprises the steps of: temporarily hiding characters in a sequential order, thereby creating a movement sensation and, thus, a visual field stimulus; and detecting the user's attempt to look at a corresponding location on the display screen currently being stimulated.

19. The method according to embodiments 1-18, further comprising the step of monitoring and recording an at least one unprovoked modification of the at least one visual parameter by the user.

20. The method according to embodiments 1-19, wherein the step of notifying the user of a possible change in their vision further comprises the step of transmitting the notification to an at least one physician device in the possession or control of a participating physician whom the user has previously chosen to receive vision assessment data from the computing device.

21. A method for objectively assessing the vision of a user using a computing device in the possession of said user, the method comprising the steps of: implementing an assessment application in memory on the computing device; calculating a distance between the computing device and an at least one eye of the user using an at least one camera in communication with the computing device; upon the assessment application being initialized on the computing device, establishing a baseline profile for the user based on a current state of an at least one visual parameter associated with a display screen of the computing device; selectively modifying the at least one visual parameter periodically; monitoring and recording the user's response to said modifications of the at least one visual parameter; comparing the user's response to said modifications of the at least one visual parameter with the baseline profile; and upon the user's response to said modifications of the at least one visual parameter exceeding a pre-defined threshold Delta value, notifying the user of a possible change in their vision.

22. A vision assessment system configured for objectively assessing the vision of a user, the system comprising: a computing device in the possession of the user, the computing device providing an assessment application residing in memory thereon; wherein, upon the assessment application being initialized on the computing device, the system is configured for: establishing a baseline profile for the user based on a current state of an at least one visual parameter associated with a display screen of the computing device; selectively modifying the at least one visual parameter periodically; monitoring and recording the user's response to said modifications of the at least one visual parameter; comparing the user's response to said modifications of the at least one visual parameter with the baseline profile; and upon the user's response to said modifications of the at least one visual parameter exceeding a pre-defined threshold Delta value, notifying the user of a possible change in their vision.

23. The vision assessment system according to embodiment 22, wherein the assessment application is configured for running as a background process in memory while an at least one other application runs on the computing device.

24. The vision assessment system according to embodiments 22-23, further comprising an at least one camera in communication with the computing device.

25. The vision assessment system according to embodiments 22-24, wherein the system is further configured for calculating a distance between the computing device and an at least one eye of the user using an at least one camera in communication with the computing device.

26. The vision assessment system according to embodiments 22-25, wherein, while calculating a distance between the computing device and an at least one eye of the user, the system is further configured for: detecting a face of the user; detecting an iris of each eye of the user; calculating a distance between the camera and the face of the user; locating a center of each iris, such that a select at least one corresponding point on each iris may be compared and measured; calculating a distance between the center of each iris; and converting the calculated distance into a standard unit of measurement using a reference object of known dimensions inside an unscaled image of an eye of the user obtained by the at least one camera.

27. The vision assessment system according to embodiments 22-26, wherein, while calculating a distance between the camera and the face of the user, the system is further configured for multiplying a focal length of the camera by an estimated height of the user's face by a resolution normalization value, and dividing the resulting product by the product of a computed face height of the user's face and a height of the camera.

28. The vision assessment system according to embodiments 22-27, wherein, while locating a center of each iris, the system is further configured for: obtaining an unscaled image of an eye of the user using the at least one camera; applying a gamma correction on the unscaled eye image; applying a Gaussian blur on the unscaled eye image; detecting circles in the unscaled eye image; deleting all circles determined to be too small, too big, or too far away from the iris; and calculating the radius of the iris by calculating the median of the radiuses of the remaining circles.

29. The vision assessment system according to embodiments 22-28, wherein, while converting the calculated distance into a standard unit of measurement, the system is further configured for using a reference object of known dimensions inside an unscaled image of an eye of the user obtained by the at least one camera.

30. The vision assessment system according to embodiments 22-29, wherein, while using a reference object of known dimensions inside an unscaled image of an eye of the user, the system is further configured for using the iris of the user.

31. The vision assessment system according to embodiments 22-30, wherein, while converting the calculated distance into a standard unit of measurement, the system is further configured for multiplying the known size of the selected reference object in millimeters by the quotient of the interpupillary distance in pixels divided by the known size of the reference object in pixels.

32. The vision assessment system according to embodiments 22-31, wherein the system is further configured for, upon detecting the presence of eyeglasses: calculating an optical axis of each lens of the eyeglasses; matching a center of each iris with the optical axis of the corresponding eyeglasses lens; and upon determining that a deviation exists between the center of each iris and the optical axis of the corresponding eyeglasses lens: determining whether the de-centered lenses are related to frame position; and determining whether the de-centered lenses are related to a misalignment of the nose bridge pads of the eyeglasses.

33. The vision assessment system according to embodiments 22-32, wherein, while establishing a baseline profile for the user based on a current state of an at least one visual parameter associated with a display screen of the computing device, the system is further configured for recording the current state of at least one of a visual parameter indicative of visual acuity, a visual parameter indicative of contrast sensitivity, a visual parameter indicative of color sensitivity, and a visual parameter indicative of visual field.

34. The vision assessment system according to embodiments 22-33, wherein, while recording the current state of a visual parameter indicative of visual acuity, the system is further configured for recording at least one of a current font type, a current font size, and a current device zoom.

35. The vision assessment system according to embodiments 22-34, wherein the system is further configured for normalizing the font size by multiplying a numerical font size by a ratio between device-independent pixels and pixels of the computing device, by the device zoom.

36. The vision assessment system according to embodiments 22-35, wherein, while recording the current state of a visual parameter indicative of contrast sensitivity, the system is further configured for recording a screen luminance of the display screen of the computing device.

37. The vision assessment system according to embodiments 22-36, wherein the system is further configured for determining a contrast resolution of the display screen by: calculating first quotient by dividing the greater of a relative luminance of a current font color and a relative luminance of a current background color, plus a value of 0.05, by the lesser of the relative luminance of the current font color and the relative luminance of the current background color, plus a value of 0.05; and calculating the contrast resolution by dividing the first quotient, minus a value of 1, by a value of 20.

38. The vision assessment system according to embodiments 22-37, wherein, while recording the current state of a visual parameter indicative of color sensitivity, the system is further configured for recording a current font color and a current background color.

39. The vision assessment system according to embodiments 22-38, wherein, while recording the current state of a visual parameter indicative of visual field, the system is further configured for temporarily hiding select of a given selection of text.

40. The vision assessment system according to embodiments 22-39, wherein, while temporarily hiding select of a given selection of text, the system is further configured for: temporarily hiding characters in a sequential order, thereby creating a movement sensation and, thus, a visual field stimulus; and detecting the user's attempt to look at a corresponding location on the display screen currently being stimulated.

41. The vision assessment system according to embodiments 22-40, wherein the system is further configured for monitoring and recording an at least one unprovoked modification of the at least one visual parameter by the user.

42. The vision assessment system according to embodiments 22-41, further comprising an at least one physician device in the possession or control of a participating physician whom the user has previously chosen to receive vision assessment data from the computing device.

43. The vision assessment system according to embodiments 22-42, wherein, while notifying the user of a possible change in their vision, the system is further configured for transmitting the notification to the at least one physician device.

In closing, regarding the exemplary embodiments of the present invention as shown and described herein, it will be appreciated that a system and associated methods for objectively assessing vision using a computing device is disclosed. Because the principles of the invention may be practiced in a number of configurations beyond those shown and described, it is to be understood that the invention is not in any way limited by the exemplary embodiments, but is generally directed to a system and associated methods for assessing vision using a computing device and is able to take numerous forms to do so without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention. Furthermore, the various features of each of the above-described embodiments may be combined in any logical manner and are intended to be included within the scope of the present invention.

Certain embodiments of the present invention are described herein, including the best mode known to the inventor(s) for carrying out the invention. Of course, variations on these described embodiments will become apparent to those of ordinary skill in the art upon reading the foregoing description. The inventor(s) expect skilled artisans to employ such variations as appropriate, and the inventor(s) intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (along with equivalent open-ended transitional phrases thereof such as "including," "containing" and "having") encompasses all the expressly recited elements, limitations, steps and/or features alone or in combination with un-recited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amendment for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim, whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (along with equivalent open-ended transitional phrases thereof) includes within its meaning, as a limiting case, claimed subject matter specified by the closed-ended transitional phrases "consisting of" or "consisting essentially of." As such, embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

It should be understood that the logic code, programs, modules, processes, methods, and the order in which the respective elements of each method are performed are purely exemplary. Depending on the implementation, they may be performed in any order or in parallel, unless indicated otherwise in the present disclosure. Further, the logic code is not related, or limited to any particular programming language, and may comprise one or more modules that execute on one or more processors in a distributed, non-distributed, or multiprocessing environment.

The methods as described above may be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multi-chip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. A method for objectively assessing the vision of a user using a computing device in the possession of said user, the method comprising the steps of:
    implementing an assessment application in memory on the computing device;
    upon the assessment application being initialized on the computing device, establishing a baseline profile for the user based on a current state of an at least one visual parameter associated with a display screen of the computing device;
    detecting a face of the user;
    detecting an iris of each eye of the user;
    calculating a distance between an at least one camera in communication with the computing device and at least one eye of the user;
    locating a center of each iris, such that a select at least one corresponding point on each iris may be compared and measured;
    calculating a distance between the center of each iris;
    converting the calculated distance between the center of each iris into a standard unit of measurement using a reference object of known dimensions inside an unscaled image of an eye of the user obtained by the at least one camera;
    selectively modifying the at least one visual parameter periodically;
    monitoring and recording the user's responses to said modifications of the at least one visual parameter;
    comparing the user's responses to said modifications of the at least one visual parameter with the baseline profile; and
    upon at least one said response exceeding a pre-defined threshold Delta value, notifying the user of a possible change in their vision.

2. The method of claim 1, wherein the step of calculating a distance between the camera and the at least one eye of the user further comprises the step of multiplying a focal length of the camera by both an estimated height of the user's face and a resolution normalization value, and dividing the resulting product by the product of a computed face height of the user's face and a height of the camera.

3. The method of claim 1, wherein the step of locating a center of each iris further comprises the steps of:
    obtaining an unscaled image of an eye of the user using the at least one camera;
    applying a gamma correction on the unscaled eye image;
    applying a Gaussian blur on the unscaled eye image;
    detecting circles in the unscaled eye image;
    deleting all circles determined to be too small, too big, or too far away from the iris; and
    calculating the radius of the iris by calculating the median of the radiuses of the remaining circles.

4. The method of claim 1, wherein the step of using a reference object of known dimensions inside an unscaled image of an eye of the user further comprises the step of using the iris of the user.

5. The method of claim 4, wherein the step of converting the calculated distance between the center of each iris into a standard unit of measurement further comprises the step of multiplying the known size of the selected reference object in millimeters by a resulting quotient of the interpupillary distance in pixels divided by the known size of the reference object in pixels.

6. The method of claim 1, further comprising the steps of detecting the presence or absence of eyeglasses; and upon detecting the presence of eyeglasses:
    calculating an optical axis of each lens of the eyeglasses;
    matching a center of each iris with the optical axis of the corresponding eyeglasses lens; and
    upon determining that a deviation exists between the center of each iris and the optical axis of the corresponding eyeglasses lens:
        determining whether the de-centered lenses are related to frame position; and
        determining whether the de-centered lenses are related to a misalignment of the nose bridge pads of the eyeglasses.

7. The method of claim 1, wherein the step of establishing a baseline profile for the user based on a current state of an at least one visual parameter associated with a display screen of the computing device, further comprises the step of recording at least one of the current state of a visual parameter indicative of visual acuity, the current state of a visual parameter indicative of contrast sensitivity, the current state of a visual parameter indicative of color sensitivity, and the current state of a visual parameter indicative of visual field.

8. The method of claim 7, wherein the step of establishing a baseline profile for the user based on a current state of an at least one visual parameter associated with a display screen of the computing device, further comprises the step of recording the current state of a visual parameter indicative of visual acuity, wherein the step of recording the current state of a visual parameter indicative of visual acuity further comprises the step of recording at least one of a current font type, a current font size, and a current device zoom.

9. The method of claim 8, further comprising the step of normalizing the font size by multiplying a numerical font size by both a ratio between device-independent pixels and pixels of the computing device, and the device zoom.

10. The method of claim 7, wherein the step of establishing a baseline profile for the user based on a current state of an at least one visual parameter associated with a display screen of the computing device, further comprises the step of recording the current state of a visual parameter indicative of contrast sensitivity, wherein the step of recording the current state of a visual parameter indicative of contrast sensitivity further comprises the step of recording a screen luminance of the display screen of the computing device.

11. The method of claim 10, further comprising the step of determining a contrast resolution of the display screen by:
calculating a first quotient by dividing the greater of a relative luminance of a current font color and a relative luminance of a current background color, plus a value of 0.05, by the lesser of the relative luminance of the current font color and the relative luminance of the current background color, plus a value of 0.05; and
calculating the contrast resolution by dividing the first quotient, minus a value of 1, by a value of 20.

12. The method of claim 7, wherein the step of establishing a baseline profile for the user based on a current state of an at least one visual parameter associated with a display screen of the computing device, further comprises the step of recording the current state of a visual parameter indicative of color sensitivity, wherein the step of recording the current state of a visual parameter indicative of color sensitivity further comprises the step of recording a current font color and a current background color.

13. The method of claim 7, wherein the step of establishing a baseline profile for the user based on a current state of an at least one visual parameter associated with a display screen of the computing device, further comprises the step of recording the current state of a visual parameter indicative of visual field, wherein the step of recording the current state of a visual parameter indicative of visual field further comprises the step of temporarily hiding select characters of a given selection of text.

14. The method of claim 13, wherein the step of temporarily hiding select characters of a given selection of text further comprises the steps of:
temporarily hiding characters in a sequential order, thereby creating a movement sensation and, thus, a visual field stimulus; and
detecting the user's attempt to look at a corresponding location on the display screen currently being stimulated.

15. The method of claim 1, wherein the step of notifying the user of a possible change in their vision further comprises the step of transmitting the notification to an at least one physician device in the possession or control of a participating physician whom the user has previously chosen to receive vision assessment data from the computing device.

16. A method for objectively assessing the vision of a user wearing eyeglasses using a computing device in the possession of said user, the method comprising the steps of:
implementing an assessment application in memory on the computing device;
calculating a distance between the computing device and an at least one eye of the user using an at least one camera in communication with the computing device;
providing the user with eyeglasses and
calculating an optical axis of each lens of the eyeglasses;
matching a center of each iris with the optical axis of the corresponding eyeglasses lens; and
upon determining that a deviation exists between the center of each iris and the optical axis of the corresponding eyeglasses lens:
determining whether the de-centered lenses are related to frame position; and
determining whether the de-centered lenses are related to a misalignment of the nose bridge pads of the eyeglasses;
upon the assessment application being initialized on the computing device, establishing a baseline profile for the user based on a current state of an at least one visual parameter associated with a display screen of the computing device;
selectively modifying the at least one visual parameter periodically;
monitoring and recording the user's responses to said modifications of the at least one visual parameter;
comparing the user's responses to said modifications of the at least one visual parameter with the baseline profile; and
upon at least one said response exceeding a pre-defined threshold Delta value, notifying the user of a possible change in their vision.

17. A vision assessment system configured for objectively assessing the vision of a user, the system comprising:
a computing device in the possession of the user, the computing device providing an assessment application residing in memory thereon; and
an at least one camera in communication with the computing device;
wherein, upon the assessment application being initialized on the computing device, the system is configured for:
establishing a baseline profile for the user based on a current state of an at least one visual parameter associated with a display screen of the computing device;
detecting a face of the user;
detecting an iris of each eye of the user;
calculating a distance between an at least one camera in communication with the computing device and at least one eye of the user;
locating a center of each iris, such that a select at least one corresponding point on each iris may be compared and measured;

calculating a distance between the center of each iris;
converting the calculated distance between the center of each iris into a standard unit of measurement using a reference object of known dimensions inside an unscaled image of an eye of the user obtained by the at least one camera;
selectively modifying the at least one visual parameter periodically;
monitoring and recording the user's responses to said modifications of the at least one visual parameter;
comparing the user's responses to said modifications of the at least one visual parameter with the baseline profile; and
upon at least one said response exceeding a pre-defined threshold Delta value, notifying the user of a possible change in their vision.

* * * * *